United States Patent [19]

Armstrong et al.

[11] 4,345,716
[45] Aug. 24, 1982

[54] SACHET

[75] Inventors: John C. Armstrong, Milton; Joseph H. O'Neil, Brewster, both of Mass.

[73] Assignee: The Pharmasol Corporation, Randolph, Mass.

[21] Appl. No.: 170,954

[22] Filed: Jul. 21, 1980

[51] Int. Cl.³ .............................................. A61L 9/04
[52] U.S. Cl. ..................................... 239/56; 428/74; 428/905
[58] Field of Search ........................... 428/74, 76, 905; 206/581; 239/36, 55, 56, 60; 128/270, 290 R

[56] References Cited
U.S. PATENT DOCUMENTS 3,623,659 11/1971 Maierson et al. .................... 239/56
4,145,184 3/1979 Brain et al. ...................... 428/905 X
4,228,954 10/1980 Rosenzweig ..................... 428/905 X Primary Examiner—Henry F. Epstein
Attorney, Agent, or Firm—Robert E. Meyer

[57] ABSTRACT

A sachet comprising a case of fabric defining an enclosure containing a stuffing of fibrous material within which is embedded a frangible capsule containing a volatile material releasable into the stuffing by fracturing the capsule.

12 Claims, 11 Drawing Figures

SACHET

BACKGROUND OF INVENTION

Sachets are generally made in the form of a case or envelope designed to contain a stuffing of fragrant material which may be some naturally-occurring substance such as pine needles, rose petals and the like or a stuffing of loosely-associated unwoven fibers impregnated with a volatile perfume fluid. The manufacturer and retailer of such items is faced with the problem that the fragrance dissipates very rapidly so that they can very well lose their fragrance entirely between the time of manufacture and sale. The consequences are an unhappy customer and loss of sales. Accordingly, the purpose of this invention is to provide a sachet which will not give up its fragrance until the customer purchases the same and releases the fragrance by manipulation on his part. Thus, the benefits derived are that there is no loss to the manufacturer, retailer or customer.

SUMMARY OF INVENTION

The sachet of the present invention comprises a pillow-shaped case defining an enclosure containing an absorbent stuffing and means embedded in the stuffing capable of emitting fragrance, said means comprising a sealed frangible capsule filled with a volatile liquid which can be released upon breaking the capsule, said capsule being breakable by squeezing and said stuffing being capable of absorbing the contents of the capsule without bleeding of the liquid from the sachet. The case is desirably comprised of a flexible, fabric sheet material such as a woven or knitted fabric and the stuffing is desirably comprised of loosely-associated unwoven fabric which may be partially felted. The capsule is comprised of glass or an equivalent frangible material and is enclosed within a flexible protective covering of material structured to be more absorbent than the stuffing and to be resistant to penetration by the shreds of broken glass when the capsule is broken.

The sachet is made by depositing covered capsules on a laminate of an outer layer of the material of the case and an inner layer of the material of the stuffing and then overlaying the covered capsule with an inner layer of the material of the stuffing and an outer layer of the material of the case and, finally, with the aid of a suitable die or its equivalent, heat-sealing and severing the composite layers about the covered capsule to the desired configuration.

This invention will now be described with reference to the accompanying drawings, wherein.

Figure 1:
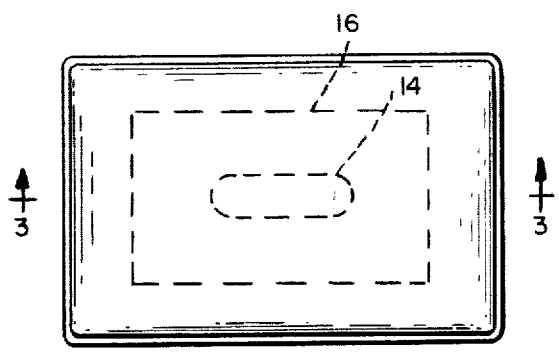
FIG. 1 is a plan view of a pillow-shaped sachet of generally rectangular configuration.
Figure 2:
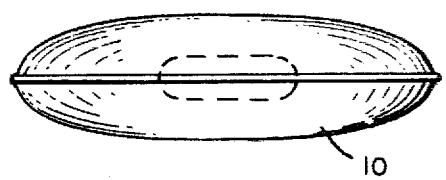
FIG. 2 is an elevation taken on the line 3—3 of FIG. 1.
Figure 3:
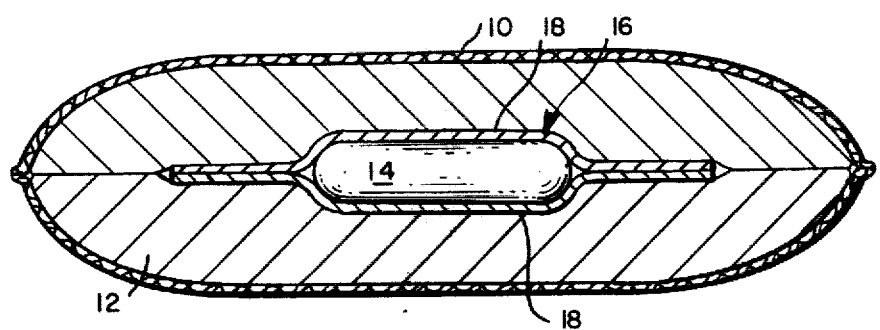
FIG. 3 is an enlarged section taken on the line 3—3 of FIG. 1.

Referring to the drawings, a typical pillow-shaped sachet is shown in FIGS. 1 to 3 comprising an outer case 10, a stuffing 12, a sealed capsule 14 containing a volatile liquid, and a covering 16 for the capsule 14.

The case 10, FIG. 3, is comprised of sheet material as, for example, a woven, non-woven, felted or knitted fabric which is relatively porous and which may be manufactured to be decorative and of pleasing appearance.

The stuffing 12, FIG. 3, is comprised of relatively loosely-associated fibers. Desirably, the fibers should be so associated that they tend to distend the case and to resiliently resist flattening thereof to thus maintain an attractive overall contour. In addition, the loosely-associated fibers which may be to a degree felted comprise an absorbent body within the case.

The capsule 14 in its preferred form is a thin glass tube sealed at its ends within which there is encapsulated a voltatile fluid such as a perfume, although it is to be understood that it could be filled with a powdered material or a frangible solid embodying in a fragrance which would be released by breaking the capsule.

Figure 4:
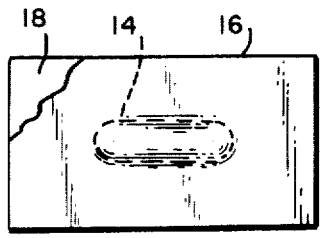
FIG. 4 is a plan view of an absorbent covering for the capsule.
Figure 6:
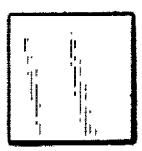
FIGS. 6, 7, 8 and 9 are plan views of pillow-shaped cases of, respectively, rectangular, circular, heart-shape and spherical shape.
Figure 7:
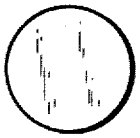
Figure 8:
Figure 9:

The capsule is embedded in the midst of the stuffing within a cover 16, FIGS. 3 and 4, which comprises two layers 18—18 of sheet material having higher absorptive characteristics that that of the stuffing. The sheet material 18—18 is both longer and wider than the capsule so as to distribute the volatile material when the capsule is broken throughout a relatively wide area and relatively uniformly throughout this area. The covering may be a sheet of blotting paper folded and sealed to include the capsule between the folds.

The sachet as thus described contained the perfume hermetically sealed within the capsule from the time that it is manufactured to the time that it is retailed to a customer in full strength so that there is no loss in potency prior to its purchase. When purchased, the customer releases the perfume by pinching the sachet so as to crush the capsule. The absorbent covering 16 is sufficiently strong, although flexible and resilient, to retain the shattered glass of the capsule and to prevent any penetration of the fragments or escape of the fragments into the stuffing. Additionally, the covering, because of its absorptive character, provides for a uniform distribution of the volatile perfume throughout the stuffing and in combination with the stuffing prevents bleeding of the liquid into and/or through the case which might discolor the case and might be detrimental to articles with which it had contact.

The sachet may be constructed in different shapes as shown, for example, in FIGS. 6, 7, 8 and 9 wherein it is variously shown as rectangular, circular, heart-shaped and spherical.

Figure 5:
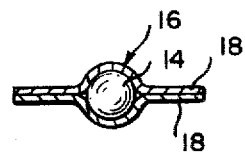
FIG. 5 is a section taken on the line 5—5 of FIG. 4.

While the capsule shown in FIG. 3 is of tube-like construction, it may be in the form of a spherical ball as shown in FIG. 5.

Figure 10:
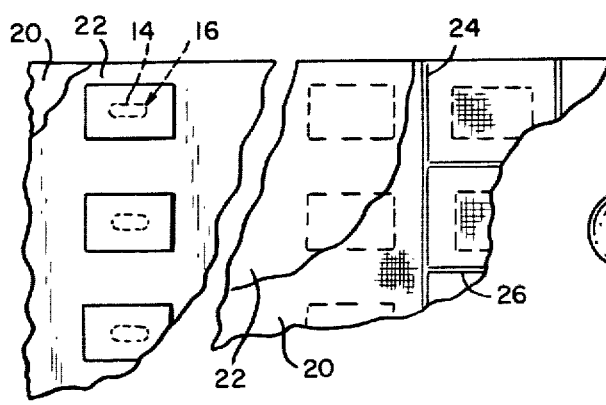
FIG. 10 is a fragmentary plan view of one method of making the sachet according to this invention.
Figure 11:
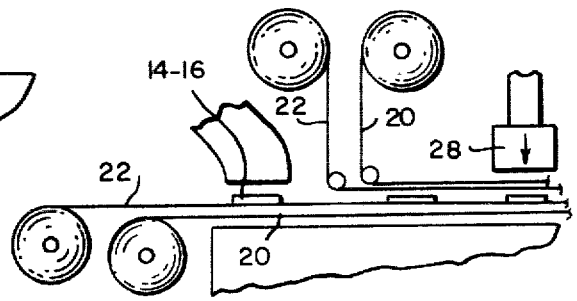
FIG. 11 is a fragmentary elevation illustrating another method of making the sachet.

The sachet may be made as shown in FIG. 10 by depositing capsules 14 with their coverings 16 on a laminate comprising an outer ply 20 of the material of the casing and an inner ply 22 of the material of the stuffing, laying over the deposited capsule and covering a laminate comprising an inner ply 22 comprised of the stuffing material and an outer ply 20 comprised of the material of the case and then sealing and severing the composite structure along rectilinearly-arranged, intersecting lines 24,26 to form individual packages of sachets. As thus formed, the stuffing is sealed about the capsule and its cover. Optionally, the sachet may be formed as shown in FIG. 11 by advancing from rolls of material an outer ply 20 of the material of the case and an inner ply of the material of the stuffing, depositing a covered capsule 14-16 on the inner ply, advancing from suitable rolls of material an inner ply 22 of the material of the stuffing and an outer ply 20 of the material of the case over the deposited covered capsule and then, by means of a heated die 28, heat-sealing and severing from the composite structure sachets of the desired configuration.

The material of the covering and stuffing may be natural or man-made fibers or a mixture thereof. If the material of the casing is comprised of man-made fibers or a mixture of man-made and natural fibers, heat-sealing can be achieved without the use of an adhesive. However, if the covering material is comprised solely of natural fibers, an adhesive must be used. The adhesive may be incorporated in the material or be pre-printed on the material in the configuration desired before assembly.

It should be understood that the present disclosure is for the purpose of illustration only and includes all modifications or improvements which fall within the scope of the appended claims.

We claim:

1. A sachet comprising a pillow-shaped case defining an enclosure, said case being comprised of two substantially coextensive sheets of porous, flexible, fabricated material joined at their edges, an absorbent stuffing constrained within the casing comprised of two substantially coextensive layers of relatively loosely associated fibers, said layers of absorbent stuffing being coextensive and in intimate surface contact with the sheets comprising the case and holding the latter distended, a covering defining a cavity within the case located between the stuffing layers, the said covering comprising coextensive plies of fibrous materials and a frangible capsule containing a volatile material positioned in the cavity between the plies of the covering, said covering and capsule positioned therein being centered with respect to the sides and edges of the case, and wherein the plies of the covering extend laterally beyond the capsule in the plane defined by the meeting surfaces of the stuffing layers a distance less than coextensive with the stuffing plies.

2. A sachet according to claim 1 wherein the covering is comprised of relatively tough absorbent material resistant to penetration of broken fragments of glass resulting from crushing the capsule.

3. A sachet according to claim 2 wherein the covering is comprised of a material which is structured to be more absorbent than the stuffing.

4. A sachet according to claim 1 wherein the configuration of the case projected in a flat plane is rectangular.

5. A sachet according to claim 1 wherein the configuration of the case projected in a flat plane is square.

6. A sachet according to claim 1 wherein the configuration of the case projected in a flat plane is circular.

7. A sachet according to claim 1 wherein the configuration of the case projcted in a flat plane is heart-shaped.

8. A sachet according to claim 1 wherein the configuration of the case projected in a flat plane is spherical.

9. A sachet according to claim 1 wherein the capsule is comprised of glass.

10. A sachet according to claim 1 wherein the capsule is a glass tube.

11. A sachet according to claim 1 wherein the capsule is a glass ball.

12. A sachet according to claim 1 wherein the capsule is comprised of a frangible plastic.

* * * * *